United States Patent
Mueller et al.

(10) Patent No.: US 6,697,453 B1
(45) Date of Patent: Feb. 24, 2004

(54) PORTABLE X-RAY DIFFRACTOMETER

(75) Inventors: Dennis William Mueller, Lake Dallas, TX (US); Russell F. Pinizzotto, Maryville, MO (US)

(73) Assignee: MetScan Technologies, LLC, Savannah, GA (US)

( * ) Notice: Subject to any disclaimer, the term of this patent is extended or adjusted under 35 U.S.C. 154(b) by 0 days.

(21) Appl. No.: 10/102,992

(22) Filed: Mar. 21, 2002

Related U.S. Application Data

(60) Provisional application No. 60/355,200, filed on Feb. 8, 2002.

(51) Int. Cl.$^7$ .............................. G01N 23/20; H05G 1/02
(52) U.S. Cl. .............................. 378/72; 378/76; 378/81; 378/198
(58) Field of Search .............................. 378/70, 71, 72, 378/73, 74, 75, 76, 79, 81, 102, 197, 198

(56) References Cited

U.S. PATENT DOCUMENTS

| | | | | |
|---|---|---|---|---|
| 4,095,103 A | * | 6/1978 | Cohen et al. | 378/72 |
| 4,489,425 A | * | 12/1984 | Borgonovi | 378/72 |
| 4,561,062 A | * | 12/1985 | Mitchell | 702/40 |
| 4,686,631 A | * | 8/1987 | Ruud | 702/42 |
| 5,068,883 A | * | 11/1991 | DeHaan et al. | 378/86 |
| 5,111,493 A | * | 5/1992 | Siedband | 378/103 |
| 5,125,016 A | * | 6/1992 | Korhonen et al. | 378/72 |
| 5,148,458 A | * | 9/1992 | Ruud | 378/72 |
| 5,155,751 A | * | 10/1992 | Chohata et al. | 378/71 |
| 5,625,664 A | * | 4/1997 | Berkeley | 378/72 |
| 6,353,656 B1 | * | 3/2002 | LeVert et al. | 378/72 |
| 6,493,420 B2 | * | 12/2002 | Ruud | 378/72 |

OTHER PUBLICATIONS

B. D. Cullity. Elements of X–Ray Diffraction, second edition (Reading, MA: Addison–Wesley), pp. 447–477).*
Paul C. Schlesselman, B.S., M.S.; Thesis: Feasibility of Using X–Ray Diffraction Linewidth for Nondestructive Evaluation: A Study of Brass; May, 1997; pp. 1–73.
Article entitled "DRS–2 Digital Radioscopy System Accessories & Options" by SAIC Products, dated Feb. 23, 2002, pp. 1–2; http://www.saic.com;products/inspection/drs2/drs2–options.html.
Article entitled "DRS–2 Digital Radioscopy System Technical Specifications" by SAIC Products, dated Feb. 23, 2002, pp. 1–2; http://www.saic.com;products/inspection/drs2/drs2–tech.html.
Article entitled "DRS–2 Digital Radioscopy System Overview" by SAIC Products, dated Feb. 23, 2002, pp. 1–2; http://www.saic.com;products/inspection/drs2/drs2.html.
Article entitled "Technologies We Develop" by SAIC, dated Feb. 23, 2002, pp. 1–2; http://www.saic.com/nde/.

* cited by examiner

Primary Examiner—Craig E. Church
Assistant Examiner—Allen C. Ho
(74) Attorney, Agent, or Firm—Thomas, Kayden, Horstemeyer & Risley, LLP

(57) ABSTRACT

In one embodiment, a portable apparatus adapted to be battery powered is used to scan an object in situ with x-rays and measure the intensity of the diffracted x-rays. The apparatus includes a scanning head having an x-ray source that is battery powered and an x-ray detector. The x-ray source and the x-ray detector are aligned in one of a plurality of predetermined alignments such that x-rays from the x-ray source are incident upon an object at a specific angle and the x-ray detector is aligned to detect x-rays that are diffracted at a specific angle, wherein the specific angle is a Bragg angle for a particular plane of atoms in the object.

40 Claims, 11 Drawing Sheets

PORTABLE X-RAY DIFFRACTOMETER

CROSS-REFERENCE TO RELATED APPLICATION

This application claims priority to co-pending U.S. provisional application entitled, "Portable X-Ray Diffractometer," having Ser. No. 60/355,200, filed Feb. 8, 2002, which is entirely incorporated herein by reference.

TECHNICAL FIELD

The present invention is generally related to the examining of the internal structure of materials and, more particularly, is related to a system and method for the non-destructive internal examination of a material.

BACKGROUND OF THE INVENTION

Metal fatigue can lead to catastrophic failure of a component or system. In power plants, oil refineries, chemical plants, or the like, metal tubes are subjected to pressures and temperatures that cause the tubes to become fatigued or to undergo creep. Metal components can also become fatigued from loading and unloading. For example, the landing struts of an airplane are subject to metal fatigue caused by the impact of landing the aircraft.

Frequently, metal components that are prone to fatigue are replaced according to a predetermined maintenance schedule, so as to avoid catastrophic failure of the metal components, which can cause the loss of life, injuries, and economic losses. However, the premature replacement of metal components can also lead to economic loss and other risks. Thus, it is desirable to examine metal components to determine their structural integrity so that they can be replaced before catastrophic failure, but not prematurely. Such an examination needs to be non-destructive.

A non-destructive method for examining the internal structure of a metal component is x-ray diffractometry. However, there have been problems associated with x-ray diffractometry outside of a controlled environment. For example, people and sensitive equipment can be harmed and damaged by being irradiated with penetrating radiation. In addition, radioactive materials, which are inherently dangerous and difficult to work with, are frequently used as sources in radiography.

Thus, it is desirable that an examination of a metal component be performned without a radioactive source. Furthermnore, it is desirable that the examination occurs in situ. In situ examination of a component can typically be done more rapidly and inexpensively than non-in situ because there it requires less disassembly and reassembly of the system. It is also desirable that the apparatus used for examining the metal component be readily transportable and adapted to be used where there is no local electricity.

Thus, a heretofore-unaddressed need exists in the industry to address the aforementioned deficiencies and inadequacies.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENTS

A brief description of x-ray diffractometry is provided hereinbelow. For further details, one can see "Introduction to Solid State Physics" Charles Kittell, John Wiley & Sons, which is hereby incorporated by reference in its entirety.

Figure 1A:
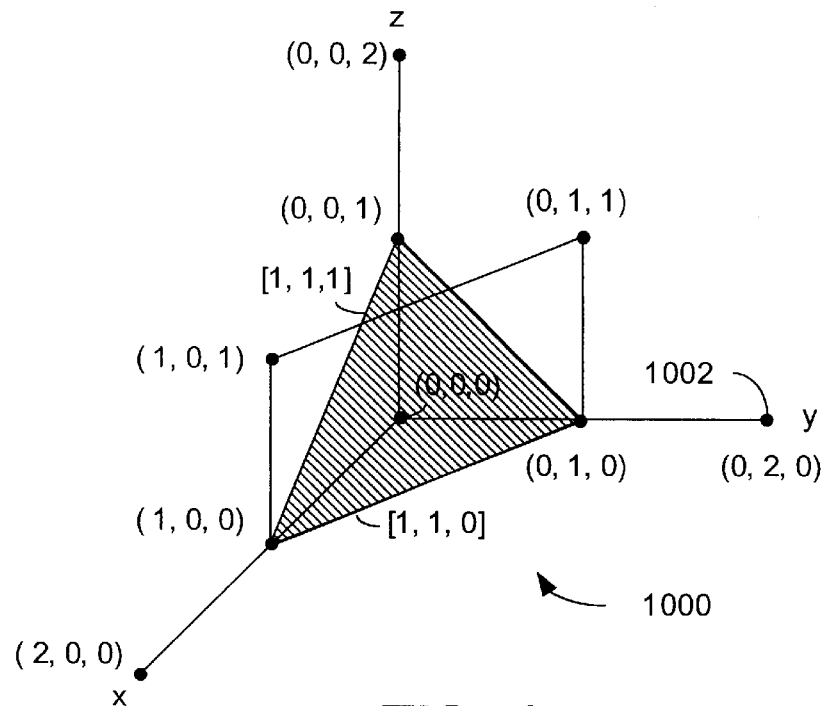
FIG. 1A is a perspective view of an exemplary crystal lattice.

Referring to FIG. 1A, a crystal 1000 is made up of atoms 1002, which are periodically repeated. The exemplary crystal 1000 shown in FIG. 1A is a cubic crystal having a lattice constant of unity. In a cubic crystal each atom 1002 has six equidistant nearest neighbors. Thus, the atom located at the origin (0,0,0) has the following nearest neighbors: ±(1,0,0), ±(0,1, 0), and ±(0,0,1). In a crystal there are many intersecting planes of atoms, and the [1,1,0] and [1,1,1] planes are shown in FIG. 1A. The [1,1,0] plane is represented by the box having atoms located at its corners, and the [1,1,1] plane is represented by the shaded triangular region having atoms located at its vertices. The designation for a plane is determined by finding the intercept of the plane with each axis (when a plane does not intersect an axis, the intercept is considered to by infinite); and then taking the reciprocals of the intercepts and reducing them to the three smallest integers having the same ratio. For example, a plane that intersects the x-axis at ½ and does not intersect the y-axis and the z-axis has the planar designation of [2,0,0]. Whereas, a plane that intercepts the x-axis at 2, the y-axis at 3, and the z-axis at 4, would be designated the [6,4,3] plane.

Figure 1B:
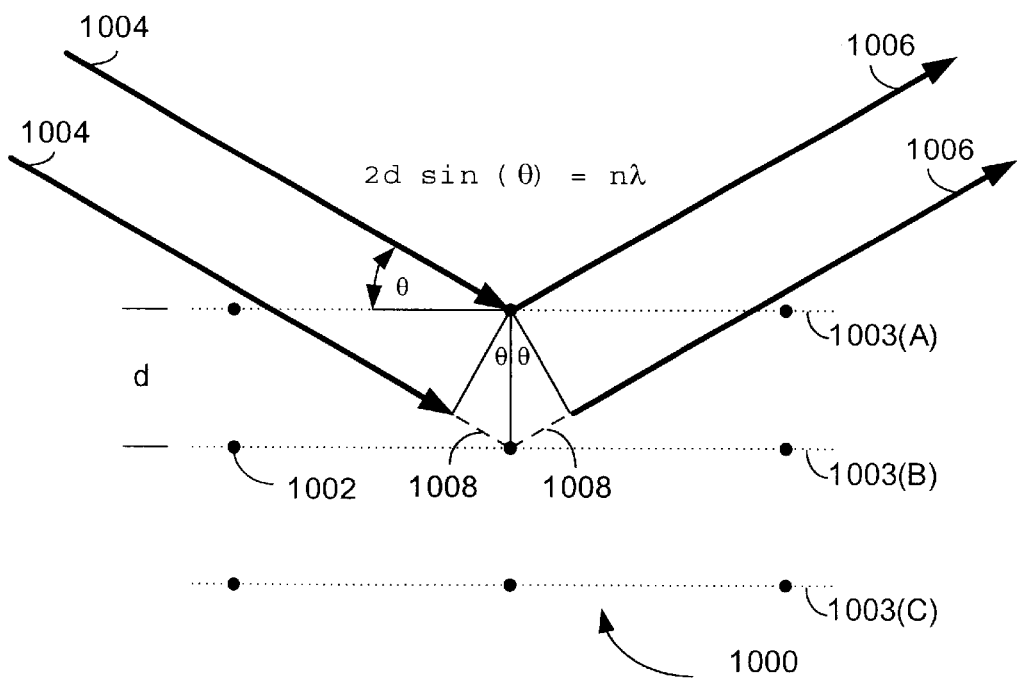
FIG. 1B is a side view of planes of atoms in a crystal diffracting incident x-rays.

Referring to FIG. 1B, the crystal 1000 includes parallel planes 1003 of atoms 1002 that are separated by a distance d. In FIG. 1B, incident x-rays 1004 are diffracted by the parallel planes 1003 of atoms 1002, which means that the angle of incidence theta equals the angle of reflection. W. L. Bragg discovered that at certain angles there are peaks in the intensity of the reflected x-rays 1006. These angles are known as Bragg angles and can be determined from the Bragg equation:

$$2d \sin(\theta) = n\lambda,$$

where d is the planar separation, θ is the angle of incidence (and reflection), and (nλ) is an integral number of wavelengths of the x-ray beam. The x-rays reflected from the second plane of atoms 1003(B) travel a different and longer path than the x-rays reflected from the first plane of atoms 1003(A). The difference in the path is shown by the dashed line 1008. Bragg's law simply relates the path difference between x-rays that are reflected from different planes to the wavelength of the x-rays. When the path difference is an integral number of wavelengths, the reflected x-rays exhibit constructive interference and a peak in the intensity is observed. Typically, a plane of atoms reflects only a small percentage of the x-rays that are incident upon it, approximately 0.001%–0.1%. Thus, incident x-rays 1004 penetrate deep into the crystal with each plane of atoms reflecting only a fraction of the incident x-rays.

In a polycrystalline material such as a metal, the material is made up of small grains of randomly oriented crystalline regions. In such a material, the incident x-rays 1004 are reflected from many grains, and because of the random orientation of the grains the incident x-ray beam 1004 is reflected in a cone. The center of the cone has an axis that is co-linear with the propagation direction of the incident x-rays. In reflected x-rays 1006 are diffracted into a cone having a central axis 1005, which is co-linear with the propagation direction of the incident x-rays 1004. Here, the angle between the central axis 1005 and the reflected beam 1006 is $2\theta$, where $\theta$ is the angle between the incident x-rays 1004 and the plane 1003 of atoms 1002 that reflect the incident x-rays 1004. In the preferred embodiment of the invention, a detector (not shown) is positioned to intersect with the cone and detect a portion of the diffracted x-rays along arc 1012. Because the grains in the polycrystalline 1010 are generally oriented in a random distribution, the intensity of the reflected x-ray beam 1006 is approximately uniform for constant values of r, i.e., along arc 1012. When the incident x-ray beam 1004 is at a Bragg angle for a given plane of the polycrystalline material 1010, there is a peak in the intensity of the diffracted x-rays 1006 along arc 1012.

Figure 2A:
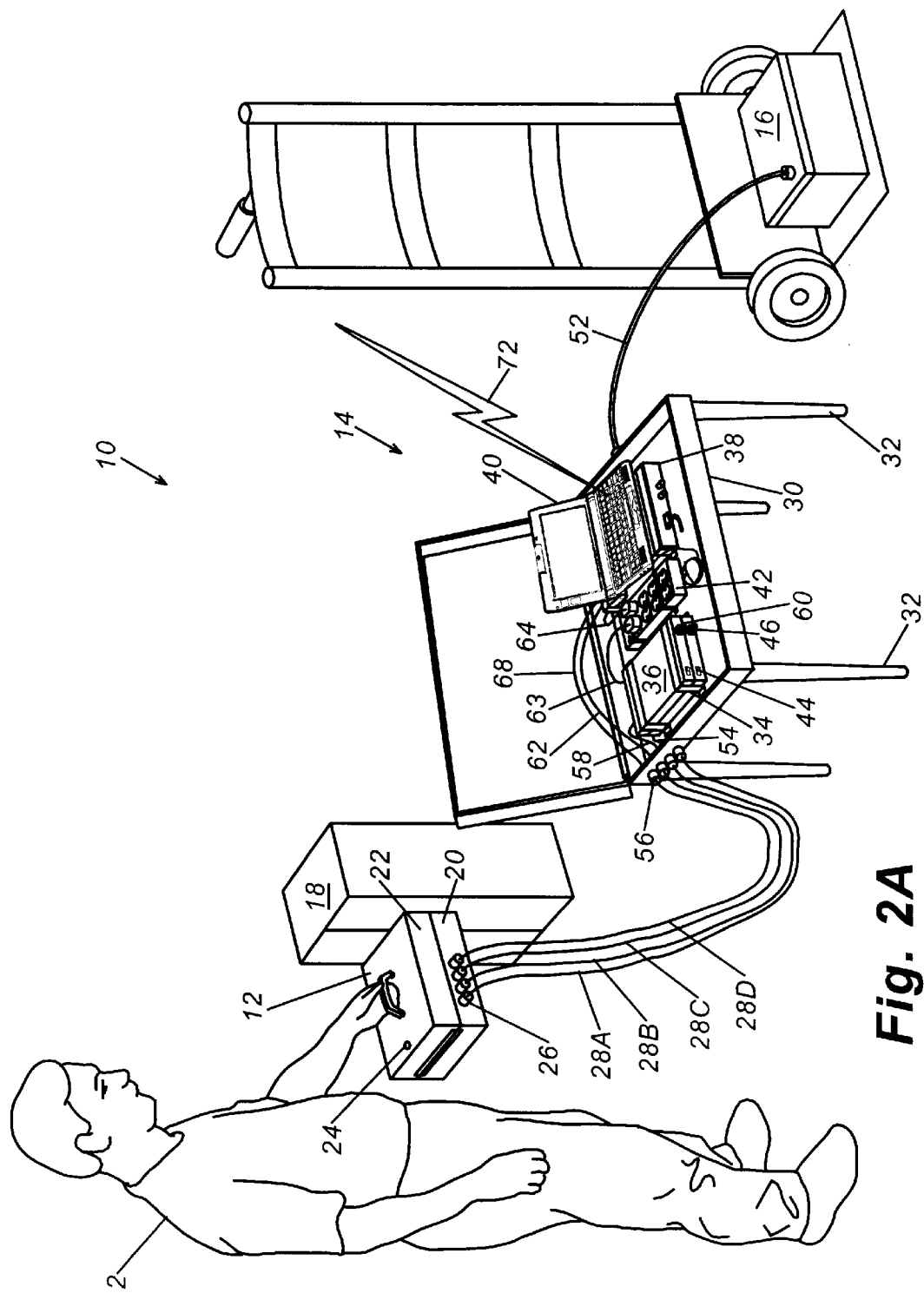
FIG. 2A is a perspective view of a portable x-ray diffractometry apparatus for examining the internal structure of an object, in accordance with one preferred embodiment of the present invention.
Figure 2B:
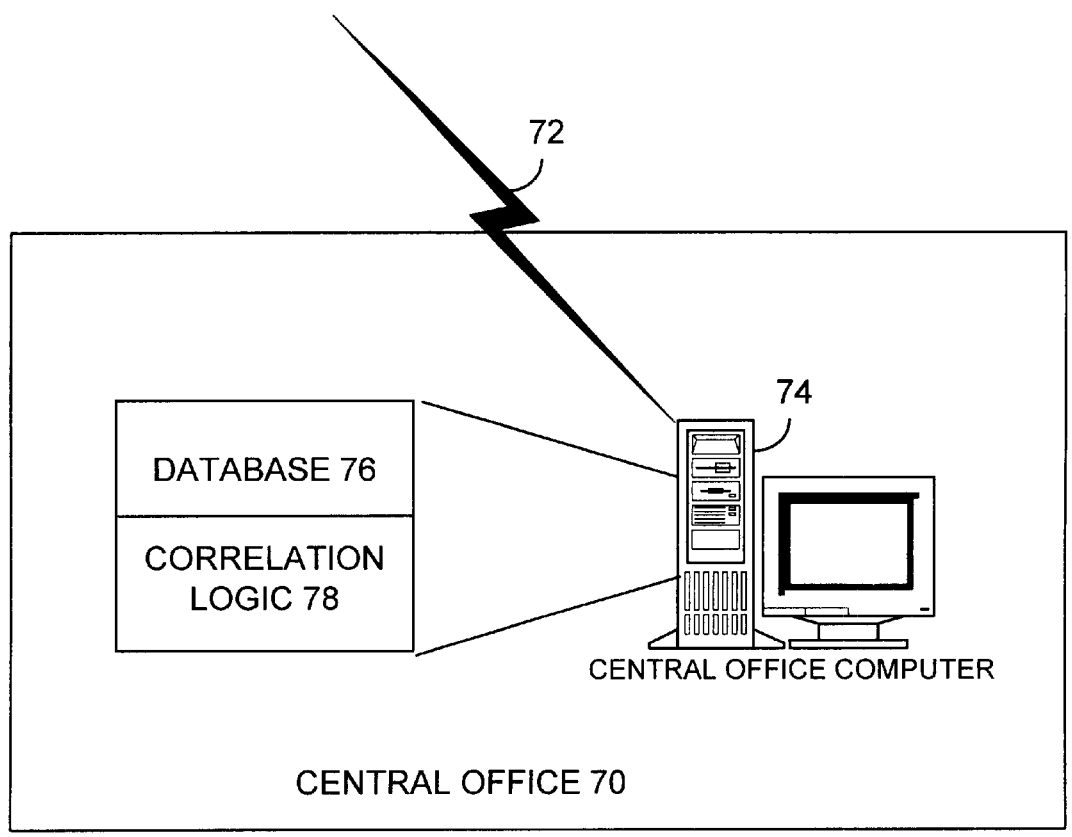
FIG. 2B is block diagram of a central office that determmines the remaining lifetime of a scanned object, in accordance with one preferred embodiment of the present invention.

Referring to FIG. 2, a Portable X-Ray Diffractometer (PXRD) assembly 10 includes two main components, a scanning head 12 and a control housing assembly 14. In one preferred embodiment, a battery 16 powers the PXRD assembly, which is typically an automotive or marine 12-volt battery. In another preferred embodiment, the battery is located within the control housing assembly 14, and in other embodiments, components are arranged in various configurations.

In operation, an operator 2 holds the scanning head 12 against an object 18. The scanning head 12 is made from an x-ray shielding material such as aluminum and is of sufficient thickness to effectively shield the operator 2 from x-rays generated from within the scanning head 12. When the scanning head 12 is in operation and positioned against the object 18, x-rays are used to scan the internal structure of the object 18 by irradiating a target area of the object with an x-ray beam and measuring the diffracted x-ray intensity.

The object 18 is generally a component of a larger system or apparatus. In a non-limiting example, the component can be a landing strut of an aircraft, or pipes or tubes in an electrical power plant or oil refinery. Typically, the PXRD assembly 10 irradiates the object 18 while the object 18 is integrated into the larger system or apparatus. Frequently, the examination of the internal structure of the object 18 is done during routine maintenance of the larger system or apparatus. In a non-limiting example, electrical power plants are frequently shut down for routine maintenance of tubes located in a boiler, the tubes carry superheated steam and are examined in situ by the PXRD assembly 10. In other situations, the PXRD assembly 10 is used to examine components of systems that are in operation. In another non-limiting example, tubes such as those found in an oil refinery or a power plant that are accessible during the operation thereof are examined in situ by the PXRD assembly 10. In yet another non-limiting example, components of systems that are idle, but not disassembled, nor in maintenance mode, such as landing struts of a parked aircraft are examined in situ by the PXRD assembly 10.

The scanning head 12 preferably includes a base 20 and a cover 22, which is pivotally coupled to the base 20 by hinges (not shown), thereby providing the operator 2 access to the components included therein. In one embodiment, the scanning head 12 also includes an LED 24, which is lit when the scanning head 12 is in scanning operation.

The exterior of the scanning head 12 preferably includes cable connectors 26, which provide coupling between internal components of the scanning head 12 and cables 28A through 28D. The internal components of the scanning head 12 are described hereinbelow.

The control housing assembly 14 preferably includes a carrying case 30 that has foldable legs 32 attached thereto. The exterior of the carrying case 30 includes a plurality of cable connectors 56, which provide coupling for the cables 28A through 28D. Inside of the carrying case 30 are components of the PXRD assembly 10, which include an x-ray source controller 34, an x-ray detector controller 36, a data processor 38, a laptop computer 40, and a power inverter 42.

The x-ray source controller 34 includes a power switch 44 and voltage and current control knobs 46. The x-ray source controller 34 is electrically coupled to the battery 16 via a power cord (not shown) that extends from the x-ray source controller 34 to a receptacle (not shown), which receives a power cord 52 that extends from the receptacle to the battery 16. The power-cord from the receptacle bifurcates such that the x-ray source controller 34 and the power inverter 42 are both in electrical communication with the battery 16. Extending from the x-ray source controller 34 to the backside of cable connectors 56 is a cable 54, which is typically a 12-wire bundle terminated with AMP CPC 17–16 type connector. The cable 54 is in electrical communication with an x-ray source (not shown) located in the scanning head 12 via cable 28A. The x-ray source controller 34 sends electrical power and control information to the x-ray source via cables 54 and 28A. The x-ray source controller 34 is configured, among other things, to initiate the operation of the x-ray source. Typically, initiation involves the x-ray source controller 34 regulating the electrical power delivered to the x-ray source such that the x-ray source is warmed up and brought to operation power in increments. In the preferred embodiment, the x-ray source controller 34 includes a plurality of LEDs that indicate whether the x-ray source controller 34 is in operation mode or warm-up mode.

The x-ray detector controller 36 is coupled to the power inverter 42 via power-cord 63 and to the cable connectors-56 via a cable 58, which is typically a Sony CCXC-12P02 camera cable. The x-ray detector controller 36 includes a control knob 60, which controls the gain of the x-ray detector (not shown), that is included in the scanning head 12. Power and control information is provided to the x-ray detector (not shown) via cable 58, which is coupled to cable 28B via cable connectors 56.

The data processor 38 is coupled to the electrical connectors 56 via cable 62, which is typically an RG6/U cable and to power inverter 42 via power-cord 64. The data processor 38 receives data from the x-ray detector (not shown) that is located in the scanning head 12, via cable 62, which is in communication with cable 28C through cable connectors 56. The data processor 38 is also coupled to the laptop computer 40 via a cable (not shown), which is typically a small computer system interface (SCSI) cable. Both the image processor 38 and the laptop computer 40 have SCSI ports for communicating.

In one preferred embodiment, the data processor 38 is adapted to receive data from the x-ray detector in the scanning head 12 and generate an image that represents the intensity of the reflected x-rays. The data processor 38 also includes an output port (not shown) for connecting a video monitor (not shown) to the data processor 38. Typically, the video monitor is a Sony monitor, such as model HPVM1354Q High Resolution RGB monitor, or the like and the video output port is a VGA port. Typically, the video monitor is used by the operator 2 for viewing the intensity of the reflected x-rays, which will be discussed in detail hereinbelow.

In one preferred embodiment, the computer 40 receives image parameters and/or data from the data processor 38 and further analyzes it using logic such as Peakfit to determine among other things the full width at half maximum of the image. The computer 40 may also include a CD burner (not shown) or DVD burner (not shown), which is used to store the data from the data processor 38 and/or other information. By storing the information on a CD or DVD or in some other medium, a snap-shot in time of the current characteristics of the object 18 is preserved. In the future, different snap-shots in time of the characteristics of the object 18 can be compared as part of the analysis or change of the internal structure of object 18.

The computer 40 is coupled to a serial cable 68 that extends from the computer 40 to the cable connectors 56. The computer 40 is in communication with a photo-spectrum analyzer located in the scanning head 12 via serial cable 68, which is in communication with cable 28D via cable connectors 56. The computer 40 receives spectral data from the photo-spectrum analyzer, which is then used to identify the composition of the object 18. Frequently, similar components of a system are replaced during the lifetime of the system, and as new alloys become available, the components are replaced with components having different alloys. The spectral characteristics of the object enables the operator 2 to identify the alloy of the object 18. In one embodiment, the computer 40 includes a database of spectral characteristics for materials so that the computer can identify the composition of the object 18.

In one preferred embodiment, the computer typically includes an input/output interface (not shown) such as, but not limited to, a modem or Ethernet card for communicating with a central office computer 74 via communication link 72 at a central office 70. The communication link 72 can be the Internet, a modem connection over a telephone system, a wireless connection, or other communication path known to those skilled in the art. Information such as, but not limited to, spectral data, image data, raw X-ray count data, line shape data/parameters, can be transmitted to the central computer 74 via communication link 72. Data from the photo-spectrum analyzer may also be stored on a CD burned by the CD burner and the CD can be provided to the central office computer 74.

Typically, the computer 40 is configured to process data from the scanning head 12 in addition to sending information to the central office computer 74. The computer 40 includes processing logic that enables it to average x-ray intensities for pixels that have the same radial distance from central axis 1005, and data fitting logic to fit data to various mathematical models, such as, but not limited to "Peakfit" by Jandel Scientific Software.

At the central office 70, the central office computer 74 receives information from the portable computer 40 and processes the information to determine among other things, the remaining lifetime of the object 18. The central office computer 74 includes database 76 and correlation logic 78. When the central office computer 74 receives information from the laptop computer 40 the central office computer 74 implements the correlation logic 78 to determine the remaining lifetime of the object 18. The database 76, includes among other things, results from crystalline analysis of test objects having crystalline and polycrystalline composition, results of structural integrity analysis of test objects, which can include both destructive and non-destructive tests, and photo-spectrum results of test objects. The correlation logic 78 analyzes the information from the laptop computer 40 and correlates the crystalline characteristics of the object 18 with the information in database 76 to determine the remaining lifetime of the object 18. Typically, the information from the laptop computer 40 includes a mathematical representation of the x-ray diffraction pattern of the object 18. The information from the laptop computer 40 can also include both composition information such as the photo-spectrum analysis of the object 18 and crystalline information of the object 18. The information from the laptop computer 40 may further include raw data from the PXRD assembly 10, or partially analyzed data, which could have been partially analyzed by the image processor 38 or by the laptop computer 40.

Figure 3:
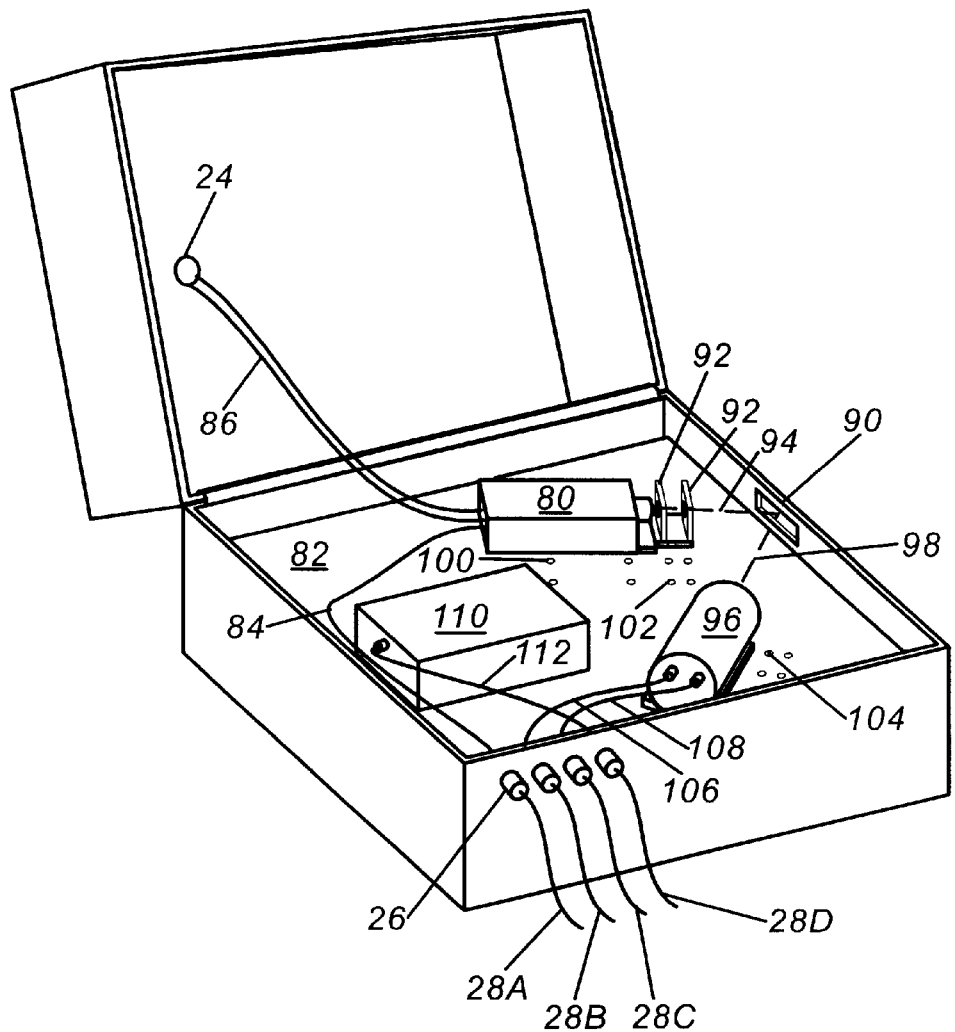
FIG. 3 is a perspective view of components in the scanning head of FIG. 2A.
Figure 4:
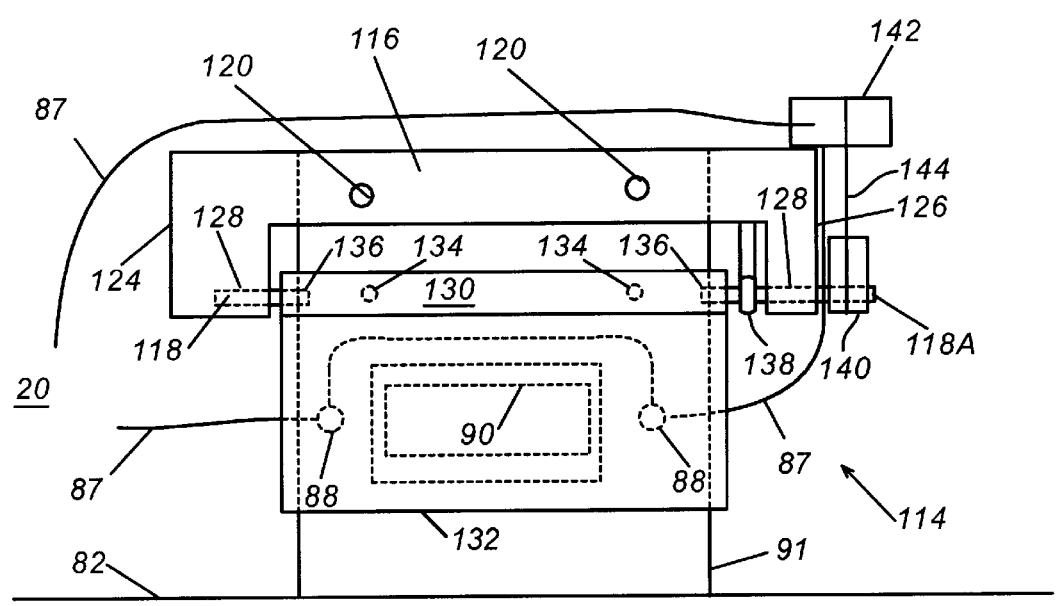
FIG. 4 is a front view of a shuttered window in the scanning head of FIG. 2A.

Refer to FIG. 3, the scanning head 12 includes an x-ray source 80 mounted to a mounting plate 82, which is mounted to the base 20 of the scanning head 12. In an alternative embodiment, the base 20 includes a bottom wall that forms the mounting plate 82.

The x-ray source 80 receives power and operating parameters from the x-ray source controller 36 via cable 84, which extends from the x-ray source 80 to cable connectors 26, where cable 84 is in communication with cable 28A. The operating parameters from the x-ray source controller 34 include current and voltage settings for regulating the intensity and energy of the x-rays generated by the x-ray source 80. The x-ray source 80 also receives signals that put the x-ray source 80 in warm-up mode and in operating mode. The LED 24 receives electrical power from the x-ray source 80 via a pair of electrical wires 86.

In operation mode, the x-ray source 80 emits x-rays that are directed at the object 18 through a window 90 that is formed in the base 20. Disposed between the window 90 and the x-ray source 80 are a pair of collimating apertures 92 that collimate the x-ray beam 94. The x-ray beam 94 is incident upon object 18 where it is then reflected into the scanning head 120.

An x-ray detector 96, receives the reflected x-rays 98. The x-ray detector 96 is mounted to the mounting plate 82 and has cables 106 and 108 extending therefrom to the cable connectors 26. Through cable 106, which is typically a Sony CCXC-12P02 camera cable, and cable 28B, which is in communication with cable 106 through cable connectors 26, the x-ray detector 96 receives operating parameters from the x-ray detector controller 36. The operating parameters include information for, among other things, setting the gain of the x-ray detector 96.

Cable 108 is in communication with cable 28C via cable connectors 26, and is used for sending x-ray data from the x-ray detector 96 to the image processor 38. In one preferred embodiment, the x-ray detector 96 is a charge-coupled device (CCD) such as a Hamamatsu Photonics CCD Camera, model number C4541 that includes a grid of pixels for detecting x-rays. When one of the pixels is struck by an x-ray, an electrical signal is produced and is associated with the pixel The x-ray detector 96 records which pixels are struck by an x-ray over a period of time, and then sends that information to the image processor 38. In an alternative embodiment, each time a pixel is struck by an x-ray, the x-ray detector 96 sends a signal that is associated with the pixel, to the data processor 38.

In one preferred embodiment, the x-ray source 80, the collimating apertures 92, and the x-ray detector 94 are removably coupled to the mounting plate 82 in a pre-defined alignment. For example, in the configuration illustrated in FIG. 2, the x-ray source 80 and collimating apertures 92 are aligned such that the angle between the x-ray beam 94 and a specific crystallographic plane of atoms in the object 18 is alpha. Similarly, the x-ray source detector 96 is aligned such that the angle between a portion of the detected reflected x-ray beam 98 and the specific crystallographic plane is also alpha. In one embodiment, the x-ray source 80 and the collimating apertures 92 and the x-ray detector 96 are each removably mounted to the mounting plate 82 by pins (not shown) extending into bores (not shown) formed in the mounting plate 82. The mounting plate 82 includes multiple bores for configuring the x-ray source 80, the collimating apertures 92, and the x-ray detector 96 in other predefined alignments. For example, in a second configuration, the pins of the x-ray source 80 and the pins of the collimating aperture are received by bores 100 and 102, respectively. Similarly, bores 104 receive the pins of the x-ray detector 96. In the second configuration, the x-ray source 80 and the collimating apertures 92 are aligned such that the angle between the incident x-rays and the reflecting plane of atoms is beta, as is the angle between a portion of the detected diffracted x-rays 98 and the reflecting plane of atoms.

The predetermined alignment of the x-ray source 80, the collimating apertures 92, and the x-ray detector 96 are determined with respect to the crystallographic characteristics of the object being scanned. In table 1, exemplary materials and the Bragg angle for specific crystallographic planes of the materials are listed for Cu Kα x-rays. In one preferred embodiment, the mounting plate 82 includes multiple alignment bores 100, 102, and 104 for aligning the x-ray source 80, the collimating apertures 92, and the x-ray detector 96 for each of the Bragg angles listed and for other Bragg angles for other materials and crystallographic planes not listed. The Bragg angle is a function of the wavelength of the x-rays and changes for x-rays of different wavelengths.

TABLE 1

| Material | Plane | Angle |
| --- | --- | --- |
| Fe | 110 | 22.3 degrees |
| Al | 200 | 22.4 degrees |
| Si | 220 | 23.7 degrees |
| Si | 111 (second order, n = 2) | 29.5 degrees |
| Fe | 200 | 32.5 degrees |
| Al | 220 | 32.6 degrees |
| Si | 400 | 34.5 degrees |

Due to the physical characteristics of the object 18, the incident x-ray beam 94 is not reflected as a collimated beam, rather, the beam is diffracted. The x-ray detector 96 is aligned such that a peak in the intensity of the diffracted x-rays 98 is observed at the approximate vertical center of the target window (not shown) of the x-ray detector 96. The scanning head 12 also includes a photo-spectrum analyzer 110, which is mounted to mounting platform 82.

When the incident x-ray beam 94 irradiates the object 18, the object 18 fluoresces, and the photo-spectrum analyzer 110 measures the intensity of the fluoresced light across a frequency range. The spectral characteristics of the object 18 are then sent to the laptop computer 40 via cable 112, which is in communication with cable 28d via cable connectors 26.

The pivotable shutter assembly 114 includes a hinge mount 116 that is rigidly affixed to the window frame 91 by a pair of mounting pins 120. The mounting pins 120 extend through the hinge mount 116 into bores (not shown) that are formed partially through the window frame 91. In alternative embodiments, the hinge mount 116 is coupled to the base 20 or to cover 22 by fastening means such as screws, bolts, rivets and other fasteners known to those skilled in the art, or by affixing means such as, but not limited to, glue or welding.

The hinge mount 116 includes opposed ends 124 and 126 that extend generally downward. Opposed ends 124 and 126 each define a bore 128 for receiving a pin 118. The bores 128 are of greater diameter than pins 118 so that the pins 118 are rotatable when in operation position. The bore 128 of end 126 extends through the end 126 so that the pin 118A extends therethrough.

The pivotal shutter assembly 114 includes a plate mount 130 and a shutter 132 rigidly coupled to the plate mount 130 by a plurality of pins 134, or other fasteners known to those skilled in the art. The plate mount 130 includes bores 136 for receiving pins 118, which are firmly pressed therein such that they are not independently rotatable.

The plate mount 130 extends between the opposed ends 124 and 126 such that the shutter 132 covers the window 90 when the shutter 132 is rotated downward. Disposed between the plate mount 130 and the end 126 of hinge mount 116 is a coil spring 138, which is firmly attached to pin 118A and to the hinge mount 116. The spring 138 is configured to apply a biasing force on pin 11 8A so that the shutter 132 is biased towards the closed position.

A cam 140 is rigidly pressed onto the pin 118A and is coupled to a solenoid 142 via a wire 144. The solenoid 142 is in electrical communication with a pair of pressure switches 88 via electrical wire 87, which extends from the x-ray source 80. In the preferred embodiment, the pressure switches 88 are connected in series so that both of the pressure switches 88 must be closed to actuate the solenoid 142. The pressure switches 88 are disposed on the exterior of the scanning head 12 proximal to the window 90 so that they are actuated when the window 90 is pressed against the object 18. In an alternative embodiment, the pair of pressure switches 88 are replaced by a single pressure switch.

In operation mode when the pressure switches 88 are closed, the solenoid 142 is actuated, thereby upwardly retracting wire 144. The upward motion of wire 144 causes the shutter 132 to rotate upward about the axis defined by pins 118, thereby uncovering window 90.

In this embodiment, the shutter 132 is made from an x-ray shielding material such as aluminum and is of sufficient thickness to effectively shield the operator 2 from x-rays generated by the x-ray source 80 by covering the window 90. If the scanning head 12 is moved such that the window 90 is no longer proximal to the object 18, then the pressure switches 88 would no longer abut the object 18 and they would not be actuated. When the pressure switches are not actuated, the solenoid 142 is not actuated and the shutter 132 is biased to cover the window 90 by the spring 138.

In one embodiment, the pressure switches 88 control power to the x-ray source 80 so that the x-ray source 80 cannot generate x-ray unless the pressure switches 88 are actuated.

Figure 5:
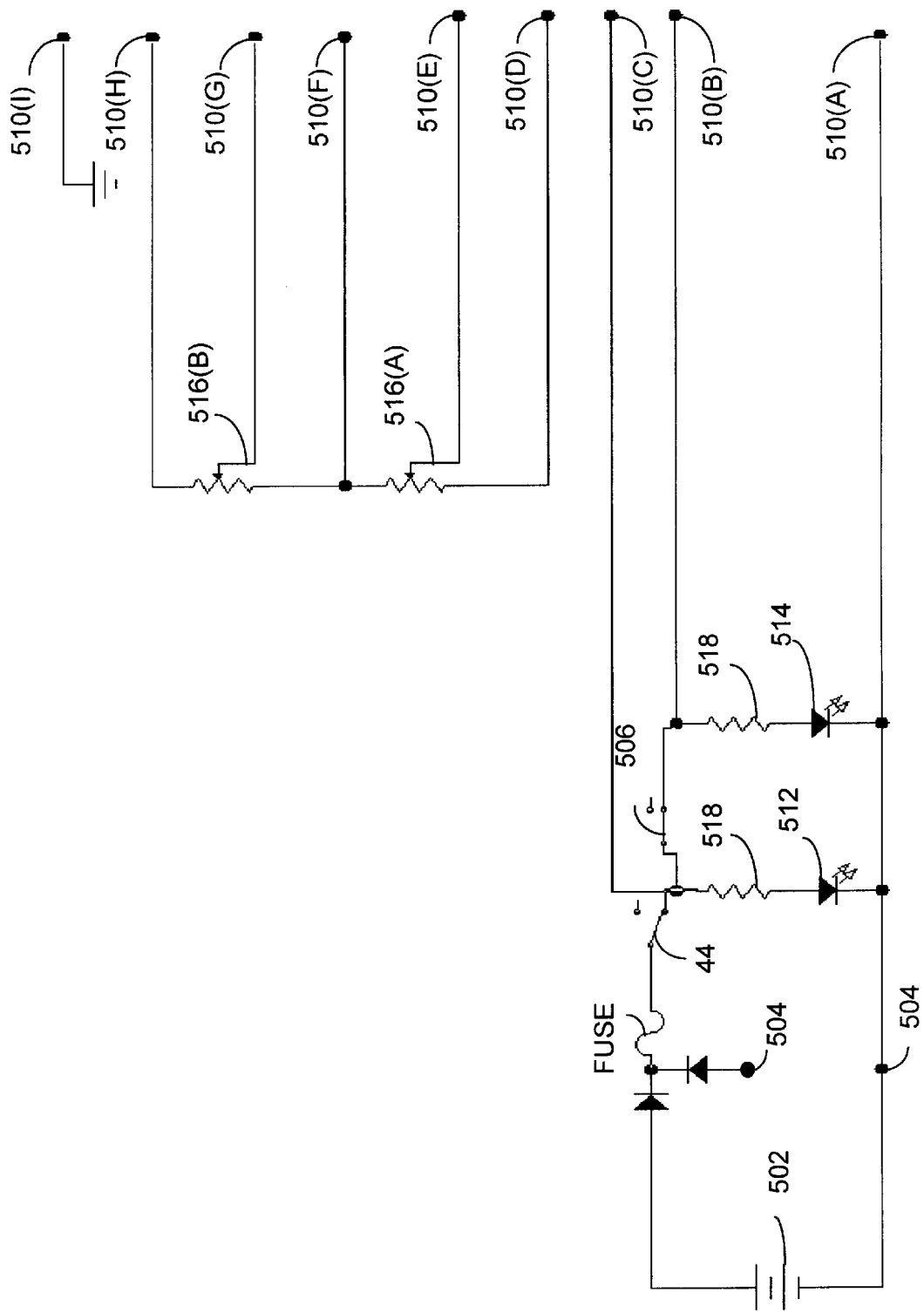
FIG. 5 is a schematic of one preferred embodiment of an x-ray source controller.

Referring to FIG. 5, the x-ray source controller 34 includes a power supply 502 that converts A/C electrical power into D/C electrical power. When A/C power is not available, the external battery 16 is connected to the nodes 504 to provide electrical power to the x-ray source controller 34. The x-ray source controller 34 includes a time delay switch 506, the power switch 44, pins 510(*a*) through 510(*i*), an LED 512 and an LED 514. Each LED 512 and 514 is in series with a resistor 518, which is typically in the 1000 Ohm range. When the power switch 44 is initially closed, the time delay switch is open and power is provided to LED 512 and to pin 510(*b*). LED 512 is used for indicating to the operator 2 that the x-ray source 80 is in warm-up mode. After a predetermined amount of time, typically around 60 seconds, the time delay switch 506 closes and power is provided to LED 514 and to pin 510(*a*). The LED 514 indicates to the operator 2 that the x-ray source 80 is now in operation mode. The pins 510(*a*) through 510(*i*) are coupled to the x-ray source 80 via cable 28(*a*). Pin 510(*a*) is the operating power pin, which is in electrical communication with the pressure switches 88 and provides the operating power to the x-ray source 80. Pin 510(*c*) is a common connector that provides a reference point for measuring potential differences and is at 12 V common.

Pins 510(*d*) through 510(*h*) are used for setting operating parameters in the x-ray source 80 using potentiometers 516(*a*) and 516(*b*), which control the current and voltage in the x-ray tube respectively. The potentiometers 516 are adjusted by the operator 2 using the control knobs 46. Adjustment of the potentiometer 516(*a*) changes the voltage between pins 510(*d*) and 510(*e*), thereby changing the current within the x-ray tube. Similarly, the adjustment of potentiometer 516(*b*) changes the voltage between pins 510(*h*) and 510(*g*) thereby changing the voltage in the x-ray tube. Pin 510(*i*) is the chassis ground pin for the x-ray source 80 and the x-ray source controller 34.

Experimental Results

In this section experimental results for an exemplary metal (brass) are given using an exemplary battery-powered x-ray diffractometer. For the experiment described herein the x-ray source was a Kevex, model no. PXS5, Cu anode x-ray source, the x-ray detector was a Hamamatsu Photonics Detector, model no. C4541 intensified CCD camera for x-ray imaging, and the data processor was a Hamamatsu Photonics, model no. C5510 Argus-20 image processing system.

Figure 6A:
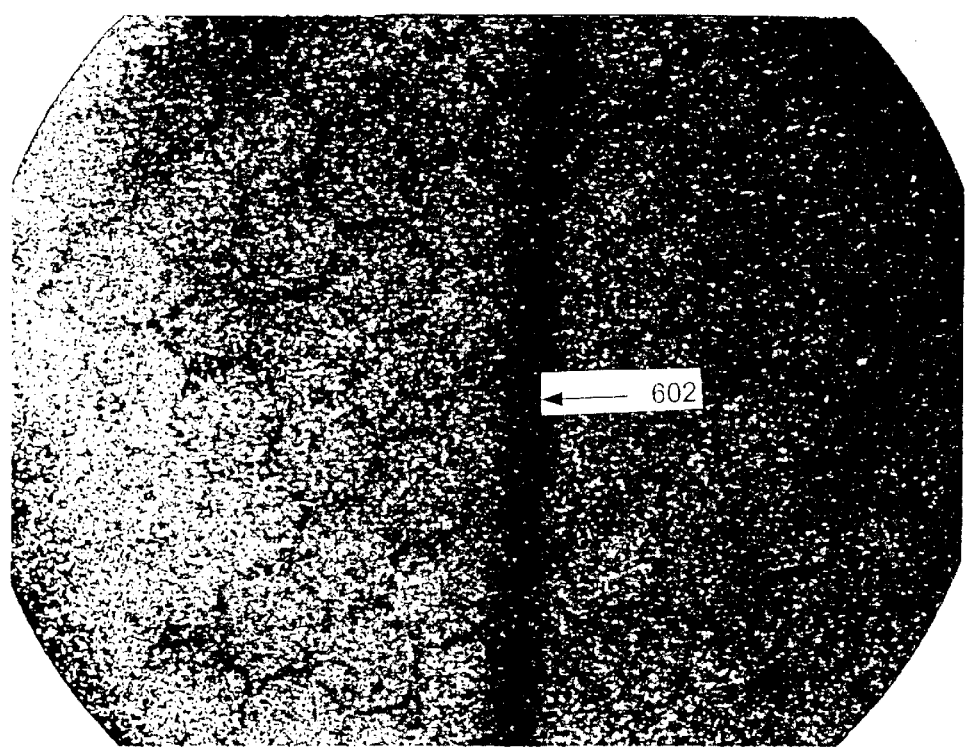
FIGS. 6A and 6B are example pictures of measured x-ray intensities.
Figure 6B:
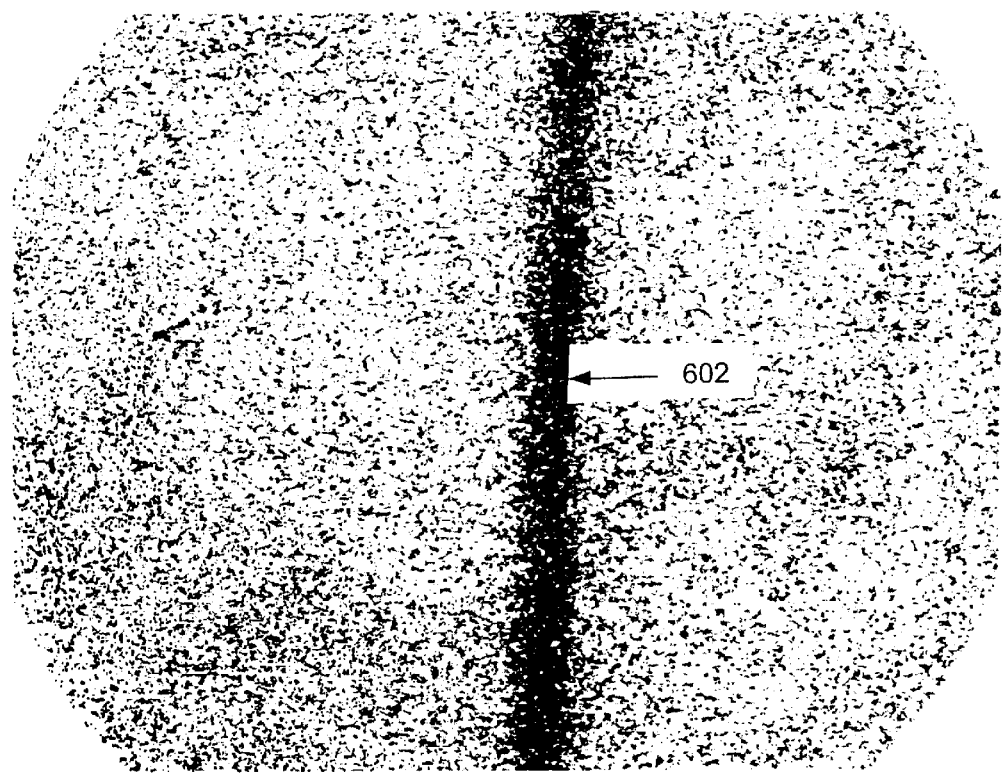
Figure 7:
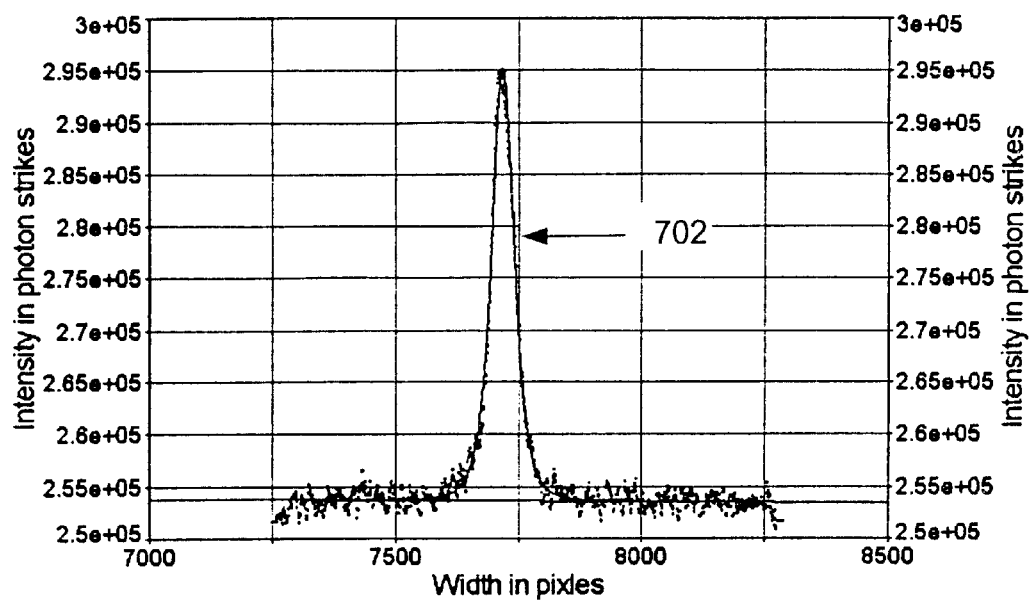
FIG. 7 is an example plot of the x-ray intensity versus radial distance.

The experimental results are shown in FIGS. 6A, 6B and FIG. 7. In this experiment, the brass specimen that was irradiated by the Kevex x-ray source for 8 hours with the x-ray source set at its maximum output. The dark vertical band 602 (shown in FIGS. 6A and 6B) which is in the approximate vertical center of the image is the detected peak in the diffracted x-ray intensity.

The x-ray detector detected x-rays using a grid of pixels. When an x-ray strikes a pixel it causes an electrical signal to be generated, which is associated with the struck pixel. Thirty times per second the x-ray detector sends the image processor data that identified which pixels had been struck in the preceding 1/30 second.

The image processor generates the image shown in FIGS. 6A and 6B by counting the number of detected x-rays for each of the pixels and associating a gray scale value for each pixel. The pixels that have the highest number of detected x-ray strikes are represented by the darkest areas in FIGS. 6A and 6B.

The image shown in FIG. 6A includes background noise, and FIG. 6B is the detected x-ray intensity with the background noise subtracted out. The background noise was caused by x-rays that were reflected into the x-ray detector from sources other than the target area of the object, i.e., the brass specimen. The background noise is related to the configuration and components used in the experiment. Thus, in one preferred embodiment, in a controlled environment, the background noise is measured in the scanning head so that the background noise can be subtracted out. The background noise for a specific alignment and configuration is determined by aligning the x-ray source 80, the x-ray detector 96, the collimating apertures 92, and the photo-spectrum analyzer 110 in the specific configuration and with the shutter window 90 uncovered and having the x-ray source 80 emit an x-ray beam through the window 90. For background noise measurements, there is no target to reflect or scatter the x-rays that pass through the window 90 back into the scanning head 12. Because there is no target, there are no fluorescent x-rays. Therefore, the x-rays that the x-ray detector 96 counts are those x-rays that are reflected off of components within the scanning head 12. Generally, the background noise is reduced by choosing the collimating apertures 92 such that the x-ray beam that exits the collimating apertures is narrow and focused upon the target area of the object 18.

Figure 1C:
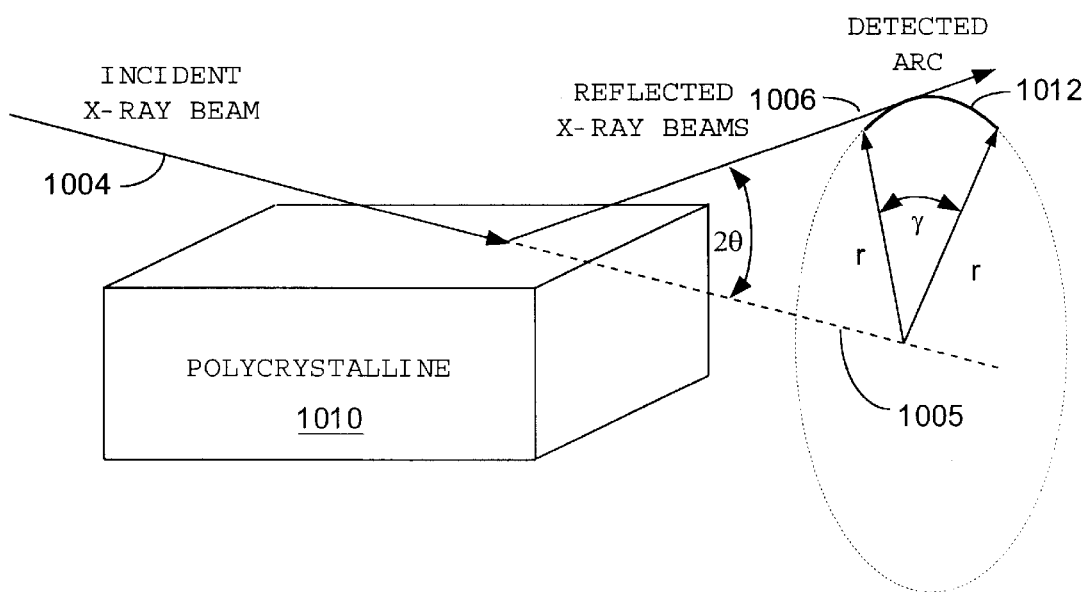
FIG. 1C a perspective view of a polycrystalline material diffracting x-rays.

Although the dark band 602 in FIGS. 6A and 6B appears approximately linear it corresponds to the arc 1012 in FIG. 1C. The x-ray intensity is processed such that the x-ray count for pixels that are the same radial distance (r) from the central axis 1005 are averaged together.

In FIG. 7 the average pixel intensity is graphed versus the radial distance from the central axis 1005. Each dot in FIG. 7 represents the average number of x-ray strikes for pixels that have the same radial distance. The solid line 702 is a parameterized fit of the data points using a Pearson VII function. In one embodiment, the data is fit using a computer program known to those skilled in the art such as Peakfit. The output of the parameterized fit includes values such as the full width at half maximum, which is used to establish a measure of the crystalline structure of the object. The width of the peak is directly related to the crystalline characteristics of the object. The more defects and imperfections in the crystal, the greater the width of the peak.

Figure 8:
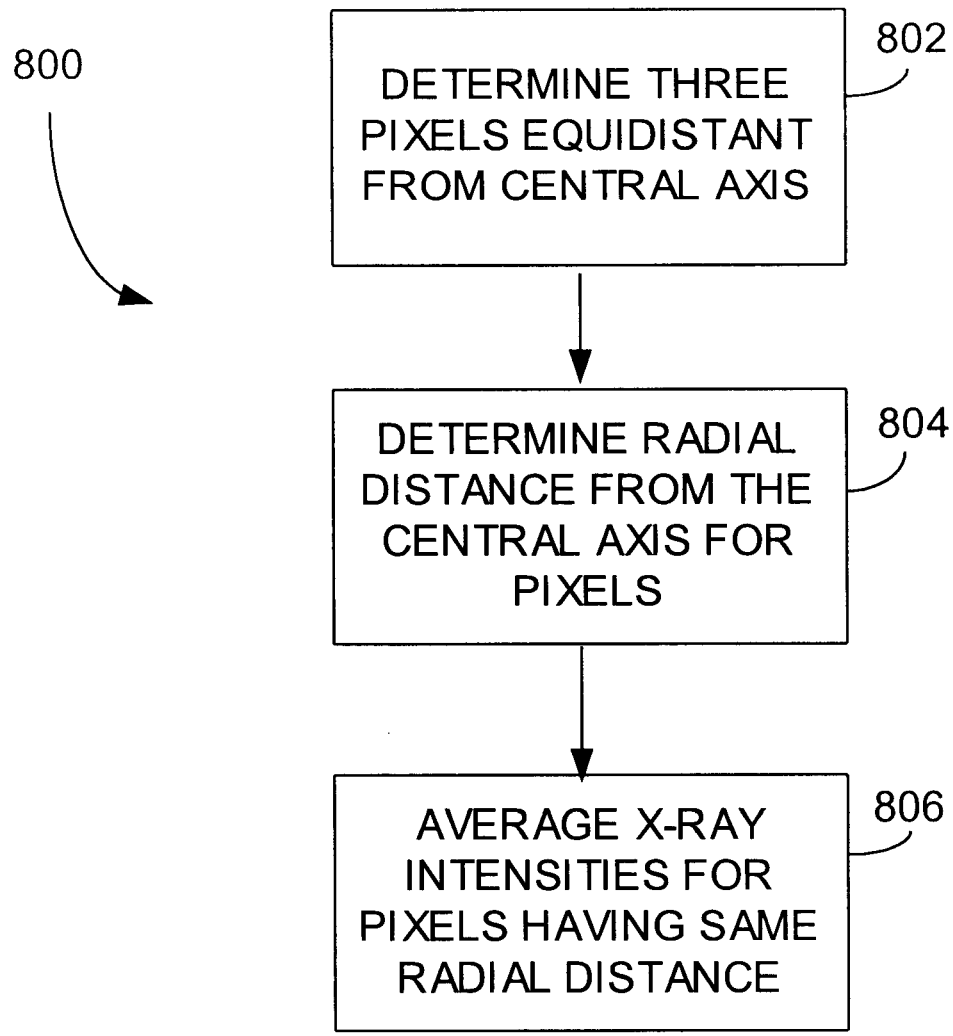
FIG. 8 is a flow chart of one example method for determining the radial distance from a central point for pixels in an x-ray detector.

Refer now to FIG. 8, steps 800 are implemented by computer 40 to average the x-ray intensities for pixels having the same radial distance from the central axis 1005. In step 802 the computer determines three pixels that are equidistant the central axis 1005. The three pixels are chosen such that they are approximately in the bottom 1/3, the middle, and the top 1/3 of the dark vertical band 602. In the preferred embodiment, the x-ray detector 80 is aligned such that the dark vertical band 602 is approximately vertical with respect to the horizontal pixels of the x-ray detector 80, and the computer 40 calculates the approximate center of the dark vertical band 602 for horizontal arrays that are in the bottom 1/3, the middle, and the top 1/3 of the pixel grid. One method for finding the approximate center of the dark vertical band 602 for a horizontal pixel array is to associate each pixel of the horizontal array with an average intensity; where the average intensity is calculated from the intensity of that pixel and a predetermined number of horizontal neighbors. The average intensity will typically be greatest in the center of the dark band 602. Thus, for each of the three horizontal pixel arrays, the computer chooses the pixel that is associated with the greatest averaged intensity and determines the radial distance from the central axis 1005 to that chosen pixel.

In step 804, the computer 40 relates the radial distance from the central axis 1005 to the three chosen pixels in terms of pixel widths and calculates the radial distance for all of the other pixels.

In step 806, the computer 40 averages the x-ray intensities of pixels that have the same radial distance from the central axis 1005. In one embodiment, the radial distance from the central axis 1005 is then related to scattering angle, the angle between the central axis 1005 and the diffracted x-ray. In that case, the line width shown in FIG. 7 would be intensity versus scattering angle.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

Therefore, having thus described the invention, at least the following is claimed:

1. An apparatus for examining the internal structure of a material, the apparatus comprising:
    an x-ray source adapted to be powered by a battery and emit an x-ray beam at the surface of a target area of the material, wherein the x-ray beam is incident upon the surface of the target area, and the angle between a particular crystallographic plane of atoms in the material and the incident x-ray beam is approximately the Bragg angle for the particular crystallographic plane;
    an x-ray detector for detecting x-rays diffracted from the target area of the material, wherein the intensity of the diffracted x-rays exhibits a peak at a given angle, as measured from the particular crystallographic plane of atoms of the material to the approximate center of the peak in intensity, and wherein the x-ray detector is aligned such that the x-ray detector receives x-rays diffracted at the given angle and the given angle is approximately the Bragg angle; and
    a mounting plate having the x-ray source and the x-ray detector rigidly coupled thereto and adapted to have the x-ray source and x-ray detector rigidly coupled thereto in multiple alignments, wherein for each of the multiple alignments the x-ray source is configured to emit an x-ray beam that is incident upon a given crystallographic plane of atoms at the Bragg angle for the given crystallographic plane and the x-ray detector is configured to detect the x-rays diffracted at the approximate Bragg angle.

2. The apparatus of claim 1, further including:
    a housing having a base and a cover pivotally coupled thereto, the base and cover defining an exterior surface with a generally hollow interior having the x-ray source and the x-ray detector mounted therein, wherein the housing defines a window extending from the hollow interior to the exterior of the housing;
    a pressure switch extending at least partially from the exterior surface of the housing, wherein the pressure switch is actuated by pressing the housing against the material proximal to the target area; and
    a movable shutter in communication with the pressure switch, wherein the movable shutter is adapted to cover and uncover the window responsive to pressure applied to the pressure switch, and wherein the housing and the shutter of sufficient thickness so as to provide substantially effective x-ray shielding from x-rays emitted from the x-ray source when the shutter covers the window.

3. The apparatus of claim 2, further including:
    a light emitting diode in electrical communication with the x-ray source, wherein the LED is adapted to be on when the x-ray source is emitting x-rays.

4. The apparatus of claim 3, wherein the LED is adapted to emit light of a first color when the x-ray source is in warm-up mode and light of a second color when the x-ray source is emitting x-rays.

5. The apparatus of claim 2, further including:
    a photo-spectrum analyzer mounted to the mounting plate and adapted to measure spectral intensity across a range of frequencies for light emitted from the target area of the material.

6. The apparatus of claim 2, further including:
    at least one electrical connector that is disposed on the surface of the housing and is adapted to removably couple with an electrical communication link.

7. The apparatus of claim 6, wherein the x-ray source is in electrical communication with the at least one electrical connector, and further including:
    an x-ray source controller in communication with the x-ray source via an electrical communication link coupled to the at least one electrical connector, the x-ray source controller adapted to provide electrical power and initiation and operation parameters to the x-ray source.

8. The apparatus of claim 7, further including:
    a storage device in electrical communication with the x-ray detector, wherein the storage device stores information related to the angular dispersion of the diffracted x-rays.

9. The apparatus of claim 2, further including:
    a photo-spectrum analyzer mounted to the mounting plate and adapted to measure spectral intensity across a range of frequencies for electromagnetic radiation emitted from the target area of the material;
    a plurality electrical connectors disposed on the surface of the housing and each of the electrical connectors is adapted to removably couple with an electrical communication link, wherein a first electrical connector of the plurality of electrical connectors is in communication with the x-ray source, a second and a third electrical connector of the plurality of electrical connectors are each in communication with the x-ray detector, and a fourth electrical connector of the plurality of electrical connectors is in communication with the photo-spectrum analyzer; and
    a control unit including:
        an x-ray source controller in electrical communication with the x-ray source via the first electrical connector, the x-ray source controller adapted to provide initiation and operation parameters and electrical power to the x-ray source;
        an x-ray detector controller in electrical communication with the x-ray detector via the second electrical connector, the x-ray detector adapted to provide electrical power and control parameters to the x-ray detector;

a data processor in electrical communication with the x-ray detector via the third electrical connector and adapted to process electrical signals associated with x-rays detected by the x-ray detector for generating information related to intensity and angular dispersion of the detected x-rays; and a computer in communication with the photo-spectrum analyzer via the fourth electrical connector and in communication with the data processor and receives the generated information related to the angular dispersion therefrom, and the computer is adapted to produce information associated with the line shape of the intensity as a function of angular dispersion for the detected x-rays, and wherein data from the photo-spectrum analyzer is used for identifying the composition of the material.

10. The apparatus of claim 9, wherein the x-ray source controller is adapted to convert AC electrical power to DC electrical power and provide DC electrical power therefrom to the x-ray source; and further including:

a power inverter adapted to convert DC electrical power from a battery to AC electrical power and provide AC power therefrom to the x-ray detector controller and the data processor.

11. The apparatus of claim 9, further including:

a database having information associated with line shapes of intensity as a function of angular dispersion for x-rays diffracted from test objects, wherein the information associated with the line shapes is further associated with the structural integrity of the test objects, and the remaining lifetime of the material is determined from correlations between the information associated with the line shape of the material and the information associated with the line shape of the test objects.

12. An apparatus for examining the internal structure of a component, the apparatus comprising:

a hand held scanning head adapted to be held against a surface of a target area of a component and irradiate the target area with x-rays generated from within the scanning head, the scanning head having an exterior surface defined by a base and a cover pivotally coupled thereto and having a generally hollow interior with a window extending from the generally hollow interior to the exterior of the scanning head, wherein the base and cover are of sufficient thickness so as to provide generally effective x-ray shielding, the scanning head including:

an x-ray source adapted to be powered from a direct current power source and generate an x-ray beam that irradiates a particular crystallographic plane of atoms in the target area at the Bragg angle for the particular crystallographic plane of atoms;

an x-ray detector adapted to count over a period of time within a given arc x-rays that are diffracted from the target area of the component, wherein the arc is a range of values that includes the Bragg angle of the particular crystallographic plane; and a mounting plate having the x-ray source and the x-ray detector removably and rigidly coupled thereto, wherein the mounting plate includes alignment bores for aligning the x-ray source and the x-ray detector in multiple predetermined alignments, wherein for each alignment the x-ray detector is aligned such that the received x-rays exhibit a peak in intensity at a particular angle and the x-ray source is aligned such that the x-ray beam is diffracted at the Bragg angle; and a controller unit, the controller unit including:

an x-ray source controller in communication with the x-ray source and adapted to provide control signals and electrical power to the x-ray source, wherein the control signals include initializing parameters that cause the x-ray source to cycle through a warm-up procedure;

an x-ray detector controller in communication with the x-ray detector and adapted to provide electrical power and control signals to the x-ray detector;

a data processor in communication with the x-ray detector and adapted to receive the x-ray measurement from the detector and generate information related to the angular dispersion of the diffracted x-rays; and a portable computer in communication with the data processor and adapted to receive the angular dispersion information and generate a measure of the crystalline characteristics of the target area.

13. The apparatus of claim 12, the apparatus further including:

a power inverter in electrical communication with the x-ray detector controller and the data processor, wherein the power inverter receives DC electrical power and converts it to AC electrical power for the x-ray detector controller and the data processor.

14. The apparatus of claim 12, wherein the portable computer is adapted to communicate with a database having lifetime data of test objects stored therein, and the measure of the crystalline characteristics of the target area is used with the database to predict the remaining lifetime of the component.

15. The apparatus of claim 12, wherein the hand held scanning head further includes:

a pressure switch actuated by pressing the window of the hand held scanning head against the target area;

a shutter in communication with the pressure switch and adapted to cover and uncover the window responsive to pressure applied to the pressure switch, wherein the shutter uncovers the window when the pressure switch is actuated and covers the window when the pressure switch is not actuated.

16. An apparatus for non-destructively examining the internal structure of a component, the apparatus comprising:

a battery powered x-ray source;

an x-ray detector; and a mounting system having the x-ray source and the x-ray detector mounted thereon, wherein the x-ray source emits an x-ray beam that is at least partially diffracted from the component, and the x-ray source and the x-ray detector are aligned such that the x-ray detector detects a peak in the intensity of the diffracted x-rays, wherein the mounting system is adapted to have the x-ray source and the x-ray detector mounted in multiple configurations, and for each configuration the x-ray source and the x-ray detector are aligned such that the x-ray detector detects a peak in the intensity of the diffracted x-rays.

17. The apparatus of claim 16, further including:

a housing having a generally hollow interior and an exterior surface, the housing defining a window extending from the interior to the exterior surface, wherein the x-ray source and the x-ray detector are disposed in the generally hollow interior.

18. The apparatus of claim 17, wherein the mounting system is an interior wall of the housing.

19. The apparatus of claim 17, wherein the mounting system includes a plate mounted to an interior wall of the housing.

20. A scanning head for non-destructively examining the internal structure of a component, the scanning head comprising:
   a housing having an exterior surface and a generally hollow interior, wherein the housing defines a window extending from the interior to the exterior surface, the window adapted to have an x-ray beam generated in the housing pass through the window;
   a pressure switch disposed on the exterior surface of the housing adapted to be actuated by abutting the housing against the component such that the window is proximal to the component; and
   a shutter assembly having a pivotal shutter disposed in the interior of the housing adapted to cover and uncover the window, wherein the shutter pivots to uncover the window when the pressure switch is actuated.

21. The scanning head of claim 20, wherein the housing and the shutter are of sufficient thickness so as to provide generally effective shielding from x-rays generated within the housing.

22. The scanning head of claim 20, wherein the x-rays are generated in the interior of the housing only when the pressure switch is actuated.

23. The scanning head of claim 20, wherein responsive to the pressure switch no longer being actuated, the generation of x-rays stops.

24. The scanning head of claim 20, wherein responsive to the pressure switch no longer being actuated, the shutter covers the window.

25. The scanning head of claim 20, further including:
   a second pressure switch disposed on the exterior of the housing proximal to a first end of the window, wherein the first pressure switch is disposed on the exterior of the housing proximal to a second end of the window and the first and second ends of the window are opposed ends.

26. The scanning head of claim 25, wherein the shutter is pivoted to uncover the window only when the first and second pressure switches are actuated.

27. A method for examining the internal structure of a component, the method comprising the steps of:
   mounting an x-ray source and an x-ray detector rigidly and removably on a mounting plate, wherein the mounting plate is adapted to have the x-ray source and x-ray detector rigidly and removably coupled thereto in multiple alignments, wherein for each of the multiple alignments the angle between the x-ray beam emitted from the x-ray source is at Bragg angle for a particular crystallographic plane of atoms and the x-ray detector is aligned to receive the diffracted x-rays at the Bragg angle;
   disposing the mounting plate with the x-ray source and x-ray detector coupled thereto in a hand held portable x-ray scanning device having a base and a cover defining a housing having a generally hollow interior, and wherein the housing is adapted to effectively shield the user from x-rays generated by x-ray source;
   irradiating a target area of a surface of a component with an x-ray beam from an x-ray source in a handheld portable x-ray scanning device, and the x-ray source is rigidly aligned in the scanning device such that the incident x-ray beam is incident upon a particular crystallographic plane of atoms at the Bragg angle for that plane;
   detecting x-rays diffracted from the target area of the component with an x-ray detector in the handheld portable x-ray scanning device, wherein the intensity of the diffracted x-rays exhibits a peak at a given angle, θ, and θ is the approximate Bragg angle for the diffracting crystallographic plane of atoms; and
   determining an indicator of the internal structure from the intensity as a function of the angular dispersion of the diffracted x-rays detected by the x-ray detector.

28. The method of claim 27, further comprising the steps of:
   enumerating the number of x-rays detected by the x-ray detector over a range of angles; and
   parameterizing the number of x-rays detected as a function of angle.

29. The method of claim 28, wherein the indicator of the internal structure is a parameter used in the parameterization of the number of x-rays counted as a function of angle.

30. The method of claim 27, wherein the x-ray source is adapted to be powered by a battery.

31. The method of claim 27, further including the step of:
   determining the remaining lifetime of the component using the internal structure indicator and a database, wherein the database includes structure indicators having lifetimes associated therewith for multiple test objects.

32. The method of claim 27, wherein the component is part of a system and is scanned in situ.

33. A method for examining the internal structure of a component, the method comprising the steps of:
   irradiating a target area of a surface of a component with an x-ray beam from an x-ray source in a handheld portable x-ray scanning device, and the x-ray source is rigidly aligned in the scanning device such that the incident x-ray beam is incident upon a particular crystallographic plane of atoms at the Bragg angle for that plane;
   detecting x-rays diffracted from the target area of the component with an x-ray detector in the handheld portable x-ray scanning device, wherein the intensity of the diffracted x-rays exhibits a peak at a given angle, θ, and θ is the approximate Bragg angle for the diffracting crystallographic plane of atoms;
   determining an indicator of the internal structure from the intensity as a function of the angular dispersion of the diffracted x-rays detected by the x-ray detector,
   measuring the spectral characteristics of the component with a photo-spectrum analyzer in the hand held x-ray scanning device, wherein the target area of the component fluoresces when irradiated by the incident x-ray beam; and
   comparing the measured spectral characteristics of the component with spectral characteristics of known materials to determine the composition of the component.

34. The method of claim 33, further comprising the steps of:
   enumerating the number of x-rays detected by the x-ray detector over a range of angles; and
   parameterizing the number of x-rays detected as a function of angle.

35. The method of claim 34, wherein the indicator of the internal structure is a parameter used in the parameterization of the number of x-rays counted as a function of angle.

36. The method of claim 33, wherein the hand held portable x-ray scanning device includes a base and a cover defining a housing having a generally hollow interior with the x-ray source and x-ray detector rigidly mounted therein, and wherein the housing is adapted to effectively shield the user from x-rays generated by x-ray source.

37. The method of claim 36, wherein the x-ray source is adapted to be powered by a battery.

38. The method of claim 36, wherein the hand held portable x-ray scanning device includes a mounting plate having the x-ray source and the x-ray detector removably mounted thereto, and the mounting plate is adapted to have the x-ray source and x-ray detector rigidly, and removably coupled thereto in multiple alignments, wherein for each of the multiple alignments the angle between the x-ray beam emitted from the x-ray source is at Brag angle for a particular crystallographic plane of atoms and the x-ray detector is aligned to receive the diffracted x-rays at the Bragg angle.

39. The method of claim 33, further including the step of:
determining the remaining lifetime of the component using the internal structure indicator and a database, wherein the database includes structure indicators having lifetimes associated therewith for multiple test objects.

40. The method of claim 33, wherein the component is part of a system and is scanned in situ.

* * * * *